(12) United States Patent
Brown (10) Patent No.: US 10,930,374 B2
(45) Date of Patent: *Feb. 23, 2021

(54) DYNAMICALLY INFERRING VARIABLE DIMENSIONS IN USER-ADDED EQUATIONS

(71) Applicant: AVEVA Software, LLC, Lake Forest, CA (US)

(72) Inventor: Harry Scott Brown, Yorba Linda, CA (US)

(73) Assignee: AVEVA Software, LLC, Lake Forest, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/411,878

(22) Filed: May 14, 2019

(65) Prior Publication Data

US 2019/0333608 A1 Oct. 31, 2019

Related U.S. Application Data

(63) Continuation of application No. 14/546,758, filed on Nov. 18, 2014, now Pat. No. 10,331,860.

(51) Int. Cl.
*G16C 20/90* (2019.01)
*G16C 20/10* (2019.01)

(52) U.S. Cl.
CPC ............. *G16C 20/90* (2019.02); *G16C 20/10* (2019.02)

(58) Field of Classification Search
None
See application file for complete search history.

(56) References Cited

U.S. PATENT DOCUMENTS

2007/0118320 A1* 5/2007 Luo ......................... G06F 30/20
702/117

* cited by examiner

*Primary Examiner* — Craig C Dorais
(74) *Attorney, Agent, or Firm* — Greenberg Traurig, LLP

(57) ABSTRACT

A processor executable method, system, and computer-readable media expedite the process of entering equations for use in developing simulations of chemical processes. The process of entering equations is expedited by dynamically inferring the dimensions of variables. The process infers the dimensions of all variables in user-added equations, and infers the dimensions of each variable in a user-added equation sequentially. The process automatically creates variables with unassigned dimensions in response to indications, such as inputs from a user, to declare new equations. The process assigns dimensions to variables based on relations between variables, such as logical relations between the dimensions of variables.

19 Claims, 6 Drawing Sheets

FIG. 1

FIG. 2A $$k = A \cdot exp\left[-\left(\frac{E_a}{RT}\right)^B\right]$$

[B] = dimensionless ← 235
[Ea] = [R]*[T] ← 240
[k] = [A] ← 245

FIG. 3

| | Variables | | | |
|---|---|---|---|---|
| | Name | Status | Type | |
| ▷ | k | ● | 1/Time ▼ | ← 335 |
| ▷ | A | ● | 1/Time ▼ | ← 340 |
| ▷ | Ea | ● | Molar Enthalpy ▼ | ← 325 |
| ▶ | T | ● | Temperature ▼ | ← 310 |
| ▷ | B | ● | Dimensionless ▼ | ← 320 |

315 points to Variables header

| | Equations | | | |
|---|---|---|---|---|
| | Name | Status | Formula | |
| ▷ | Eqn1 | ● | k = A*exp(-(Ea/R*T)^B) | ← 305 |
| ▶ | Eqn2 | ● | der(C) = k * C | ← 330 |

$$Y + X + A * \operatorname{Cos}(X * Y/Z) = 0$$

FIG. 6A

| Type your equation:<br>Y + X + A* | |
|---|---|
| Variable | Dimension |
| Y | Length |
| X | Length |
| A | |

603 → Y row; 609 → X row; 615 → A row
606 → Length (Y); 612 → Length (X); 618 → (A, blank)

FIG. 6B

| Type your equation:<br>Y + X + A*Cos(X*Y/Z) | |
|---|---|
| Variable | Dimension |
| Y | Length |
| X | Length |
| A | |
| Z | Length^2 |

606 ← header; 624 → Z row; 627 ← Length^2

FIG. 6C

| Type your equation:<br>Y + X + A*Cos(X*Y/Z)= | |
|---|---|
| Variable | Dimension |
| Y | Length |
| X | Length |
| A | Length |
| Z | Length^2 |

630 ← header; 633 → A row; 636 ← Length (A)

US 10,930,374 B2

DYNAMICALLY INFERRING VARIABLE DIMENSIONS IN USER-ADDED EQUATIONS

BACKGROUND

Conventional computer programming languages include algebraic modeling languages that allow for a user to enter equations consisting of numeric and symbolic terms. Entering and solving algebraic equations using software tools such as simulation software requires the user to work with variables. Traditionally, to work with variables, the user must define specific features of the variable to enable the computer program to work with the variable as the program executes. The user accomplishes this by declaring the variable, which at a minimum requires naming the variable and designating the dimension (e.g. length, time, mass) of the variable.

Process simulators typically have a standard library of equipment models such as pumps, valves, flowmeters, reactors, and the like that are accessed by users to build a model of their process. But if the user requires an equipment model that is non-standard or is related to a proprietary process, the equipment model is not present in the model library. This requires the user to describe the equipment model by, among other things, entering the equations and variables that describe the physics and chemistry of the process that relates to the equipment model. Describing the equipment model in this fashion can be tedious and error prone, and any help the simulator can provide to reduce user-error saves significant troubleshooting time.

Currently, interactive error messages can be provided to the user when an equation is dimensionally inconsistent. However, inferring the dimension of the variable currently requires the variable in question to exist on one side of an equation, and requires each individual variable and each dimension on the other side of the equation to be defined. Furthermore, to correct an error based on a dimension mismatch, the user may still have to search the equation extensively to determine whether the source of the error is in the equation (e.g., the user added two variables instead of multiplying them) or due to an erroneously entered variable. This is a difficult task, especially in the case where extensive algebraic equations modeling complicated processes are involved.

SUMMARY

Aspects of the present invention relate to generating improvements in simulations for use in a chemical process simulator. In an aspect, the names of variables are automatically declared and their dimensions are automatically assigned as the user enters algebraic equations and the like for generating a simulation. Variables are created based on the equation text and dimensions of the variables are dynamically inferred based on information in the equation.

In one form, a system embodying aspects of the invention dynamically infers the dimensions of variables in user-added equations, as well as sequentially infers the dimensions of each variable in a user-added equation. Variables are created from the text of an equation. In an aspect, the text takes the form of input entered by a user. The system reduces the possibility that certain errors, such as typographical errors entered by the user, result in erroneous calculations. The system reduces this possibility, for example, by using relations such as logical relations to automatically assign dimensions to variables.

In another form, a processor-executable method is provided.

In yet another form, software instructions are stored on one or more tangible, non-transitory computer-readable media and are executable by a processor.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Aspects of the present invention permit creation and editing of variables in equations for use by simulation software executed by computerized systems that provide supervisory level control of networked computerized systems in a process control system.

Figure 1:
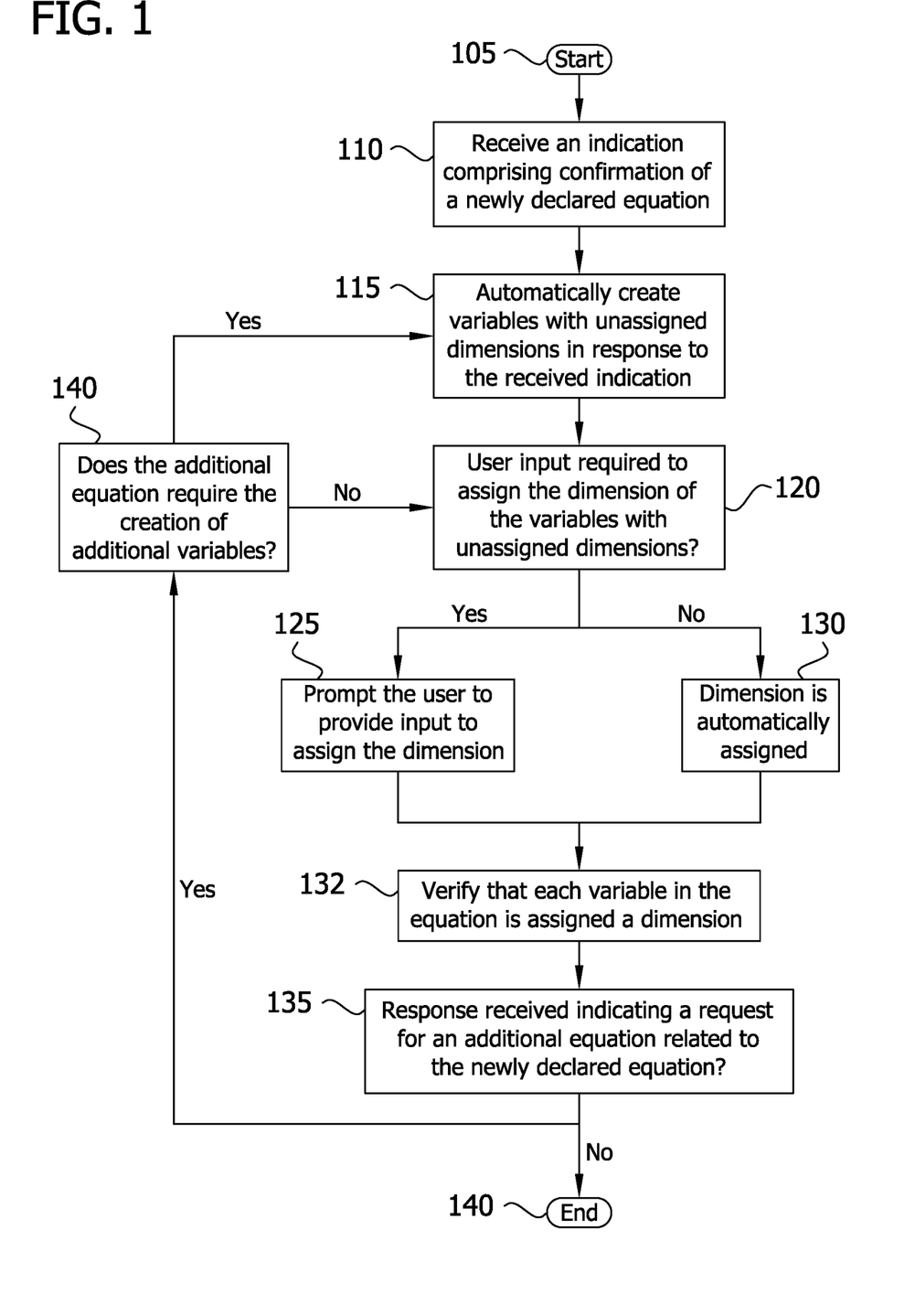
FIG. 1 is an exemplary flow diagram depicting the process by which the dimensions of all newly declared variables in a user-added equation are automatically inferred.

FIG. 1 is an exemplary flow chart diagram that illustrates the process by which the dimensions of newly declared variables in a user-added equation are automatically inferred. After the start 105 of the process, an indication is received at 110. In an embodiment, the indication comprises confirmation of a newly added or declared equation. The receipt of this indication is also known as "committing" a new equation. The receipt of the indication occurs when, for example, a user completes an equation in a designated space of a user interface by typing the equation on a keyboard and pressing the ENTER key. In another embodiment, the entry and completion of the equation is automated. In yet another embodiment, each equation is arranged in a designated column of a table on a user interface and assigned a name. In a further embodiment, the designated column is labeled "Name." In an additional embodiment, the formula to which the name of the equation refers is arranged in a second column corresponding to the column containing the names of the equations. In another embodiment, the second column is labeled "Formula."

At 115, in response to the received indication from the user, variables with unassigned dimensions are automatically created. In an embodiment, the variable is created from the text of an equation. In an embodiment, the automatically created variables are arranged in a designated column of a table on a user interface. In another embodiment, the column is labeled "Name."

Referring further to FIG. 1, the process determines at 120 whether user input is required to assign the dimension of the variable. In an embodiment, the determination is based upon logical relations between variable dimensions. If user input is required, the user is prompted to provide input to assist in assigning the dimension of the variable. One basis for making an inference is that every term in the equation must have the same dimensions. In the case where an equation includes algebraic expressions consisting of a product of numerals and variables, aspects of the invention provide the capability of postponing a variable's dimension assignment. The dimension assignment is postponed until enough equation text is entered to definitively determine the dimension of the variable. In this manner, the user is able to bypass the variable creation process altogether.

In an embodiment, the input for assigning the dimension of the variable takes the form of a user selecting from a drop-down menu to assign the dimension. In another embodiment, the drop down menu is populated with a series of selections, such as "Temperature" and "Dimensionless." In yet another embodiment, a drop down menu is allocated to each automatically created variable and arranged in a column. In a further embodiment, the column is labeled "Type."

If user input is not required to assign the dimension of the variable, the process continues at 130, where the dimension of the variable is automatically assigned. In an embodiment, the variable is automatically assigned based upon logical relations between variable dimensions in the newly added equation. At step 132, the process verifies that each variable in the equation is assigned a dimension. In an embodiment, the verification is based upon logical relations between variable dimensions. At step 135, the process determines whether a response from the user has been received that indicates a request for an additional equation related to the first equation. In another embodiment, the received response takes the form of a user further assigning a variable or a group of variables in terms of an additional equation, comprising additional variables. In yet another embodiment, the received response takes the form of an automatic determination made by the process, based upon the variables of the first equation, the variables of the additional equation, and/or other factors.

If the process determines a response has been received at 135, the process continues at 140, where a determination is made as to whether the additional equation in turn requires the creation of additional variables. If so, the process returns to 115, where additional variables with unassigned dimensions are created in response to the determination. If the process determines a response has not been received, the process ends at 145. If the additional equation does not require the creation of additional variables, the process returns to 120 and continues.

Figure 2A:
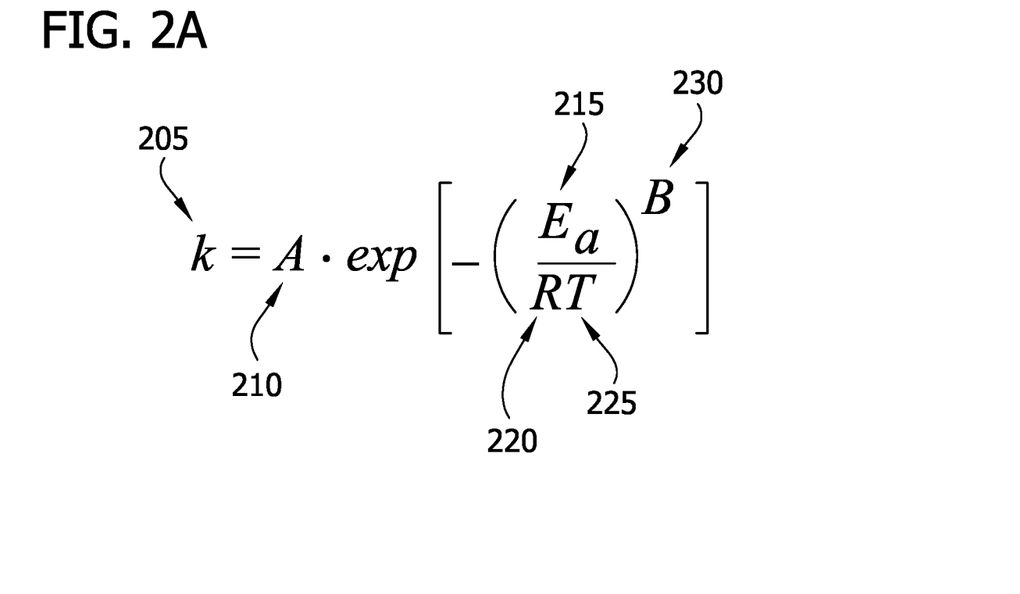
FIGS. 2A-2B depict an exemplary equation and variables of the exemplary equation, used to demonstrate aspects of the present invention.

For purposes of illustration, FIG. 2A depicts the well-known Arrhenius equation, which is a formula describing reaction kinetics in a chemical reaction. The Arrhenius equation describes the temperature dependence of the rates of reactions and is an example of an equation that a user may enter to describe an equipment model such as a reactor. The equation is used for purposes of demonstrating aspects of the present invention only; in other embodiments, other equations are contemplated for use with the present invention.

The Arrhenius equation is exemplary of the type of equation, which includes a number of variables, representative of the physics and chemistry of the process relating to an equipment model such as a reactor. As previously described, basic equipment models such as pumps and valves are typically provided through a standard library of a process simulator. However, if the equipment model, such as a reactor, is not provided, the equations and variables describing the equipment model must be entered by the user. Adding equations such as the Arrhenius equation, which includes variables with unassigned dimensions in an embodiment, requires the user to determine the dimensions of the variables, which can be an error prone and time consuming process. Any help the simulator can provide to eliminate the need for the user to enter the dimensions of variables in equations such as the Arrhenius equation, will save significant troubleshooting time.

In the example of FIG. 2A, "k" is designated at 205, "A" is designated at 210, "Ea" is designated at 215, "R" is designated at 220, "T" is designated at 225, and "B" is designated at 230. In this instance, "R" represents the ideal gas constant and the dimension need not be specified by the user because it is known.

Figure 2B:
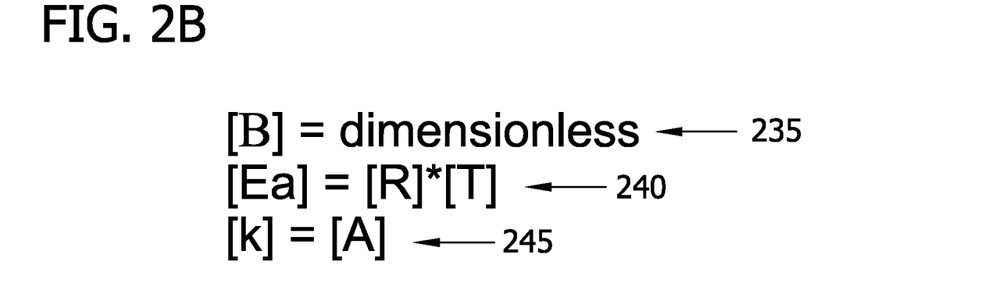

FIG. 2B is an illustration depicting the dimensions of variables illustrated in 2A, in one embodiment of the present invention. It should be understood that the use of brackets such as "[B]" as provided by the figure refer to "the dimension of B." At 235, the variable "B" is designated as dimensionless. At 240, "Ea" is designated as equal in dimension to the variable "R" multiplied by the variable "T". Finally, at 245, the variable "k" is designated as equal to the variable "A".

Figure 3:
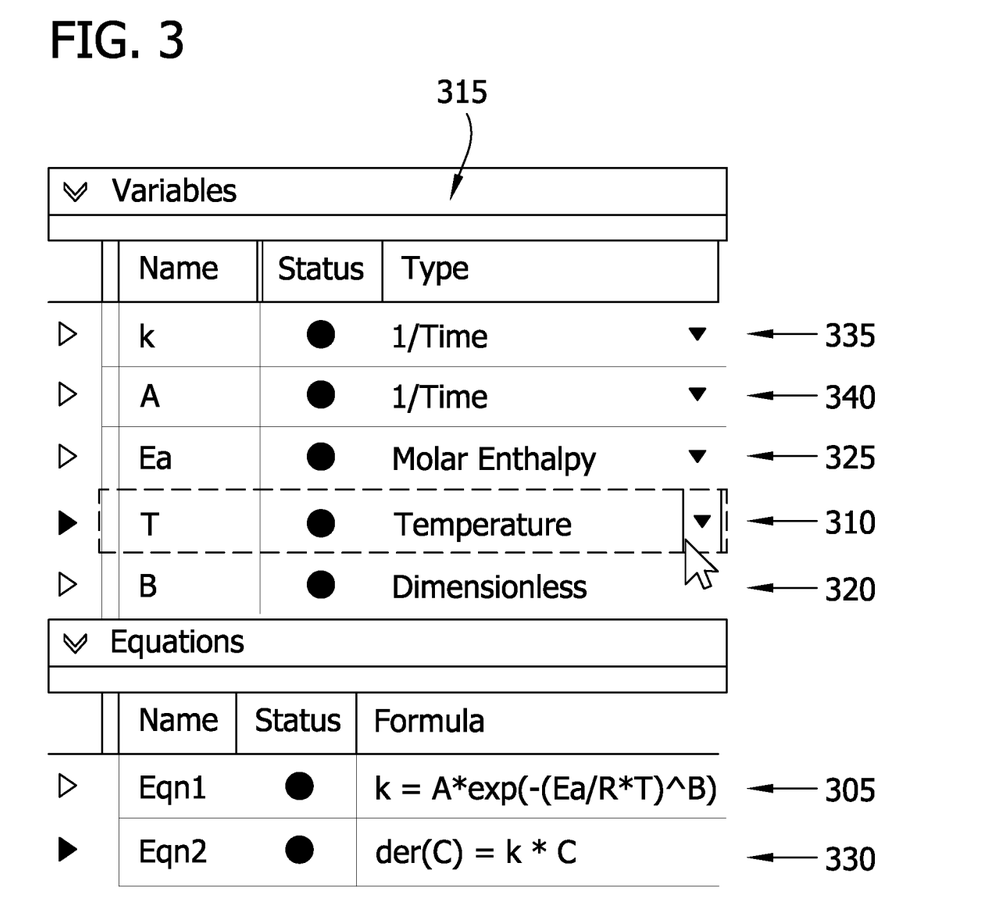
FIG. 3 is a screenshot depicting a table displayed by a user interface in accordance with one aspect of the present invention.

FIG. 3 is an exemplary screenshot depicting a table provided by a user interface embodying aspects of the invention, after completing the process illustrated by FIG. 1 in accordance with one embodiment. A newly added equation is entered at a pre-designated area 305 of the table. After an indication comprising confirmation of the new equation has been received (also known as "committing" the new equation), a determination is made as to whether user input is required to assign the dimension of the variable. If so, a user is prompted to select from a drop down menu to choose a dimension such as temperature 310 in a column dedicated to the type 315 of the designated dimension. Because the dimensions of the variables "T" 310 and "R" are known, the dimension of "Ea" 325 can be automatically assigned. It should be understood that R is not shown in the depicted table because it is a known constant that the math system has predefined (analogous to pi=3.14).

If an additional equation related to the first equation is required, such as the reaction equation related to the Arrhenius equation previously entered in the pre-designated area 305, the equation can be newly declared as an additional formula in an additional pre-designated area 330 of the table. In the instance where user input is not required to assign the dimensions of the variables in the equation related to the first equation, such as, for example, the dimension types assigned to "k" 335 and "A" 340, the dimensions of the variables are automatically assigned.

Figure 4:
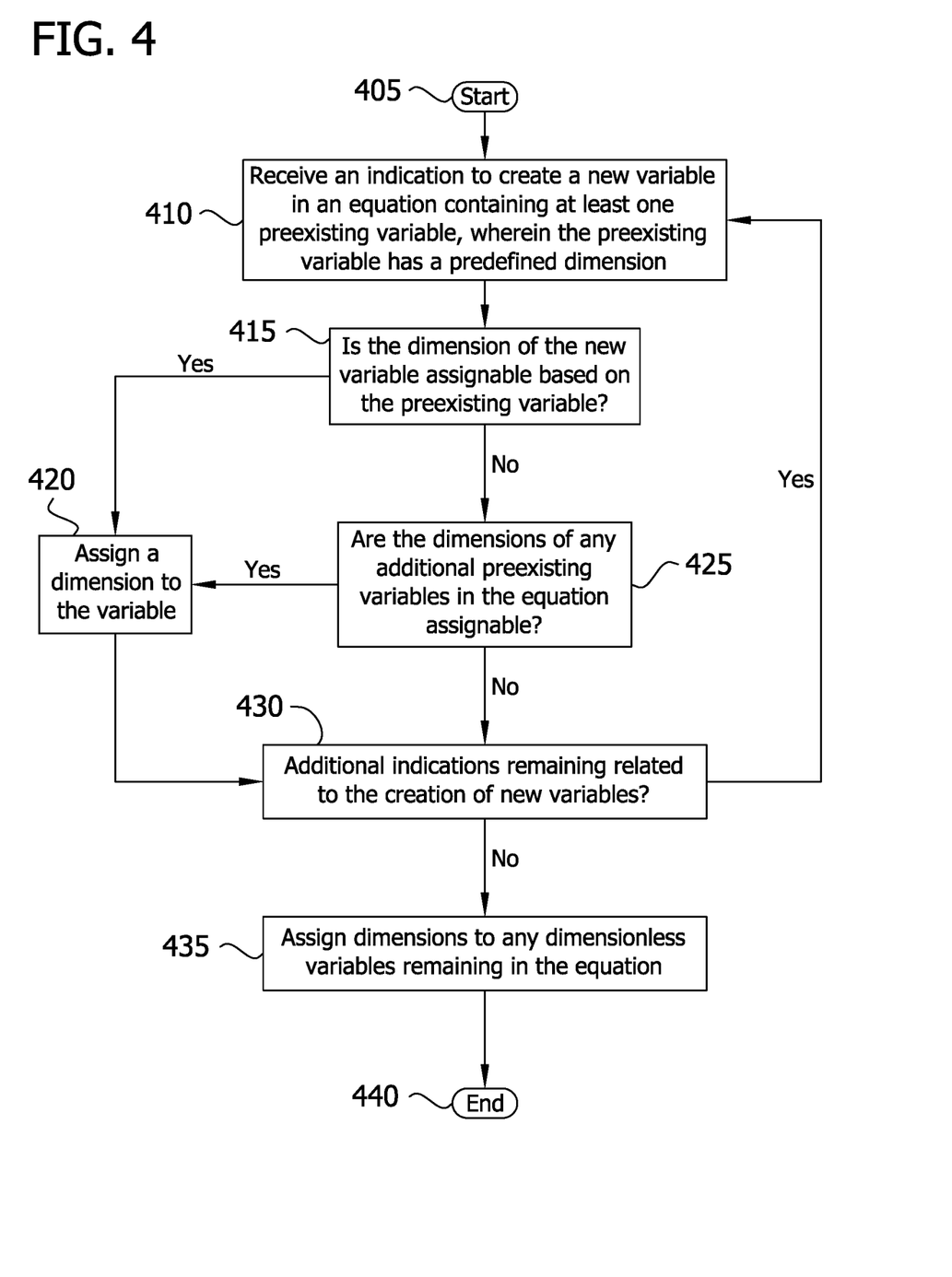
FIG. 4 is an exemplary flow diagram depicting the process by which the dimensions of each newly declared variable in a user-added equation is automatically inferred sequentially.

FIG. 4 is an exemplary flow chart diagram that illustrates the process by which the dimension of each variable in a user-added equation is automatically determined. The process starts at 405. At 410, an indication is received to create a new variable in an equation containing at least one preexisting variable, wherein the preexisting variable has a predefined dimension. In an embodiment, the variable is created from the text of an equation. At 415, a determination is made as to whether the dimension of the new variable is assignable based on the preexisting variable. If so, a dimension to the variable is assigned at 420. If not, the process continues to 425, where a determination is made as to whether the dimensions of any additional preexisting variables in the equation are assignable. In an embodiment, this condition exists if a) more than one preexisting variable was present in the equation at the time the indication 420 was received, and b) that variable's dimension was not assigned. In an embodiment, the determination 425 is made based upon examining the dimensions of the preexisting variables, and applying logical relations to the preexisting variables and the new variable.

If the dimensions of any preexisting variables in the equation are assignable, the process returns to 420 where a dimension is assigned to the variable. If the dimensions are not assignable, the process continues to 430, where a determination is made as to whether additional indications remain related to the creation of new variables in the equation. In an embodiment, the additional indications take the form of the user continuing to enter the equation using a keyboard. If so, the process returns to 410. If not, dimensions are assigned to dimensionless variables remaining in the equation at 435, and the process ends at 440.

Figure 5:
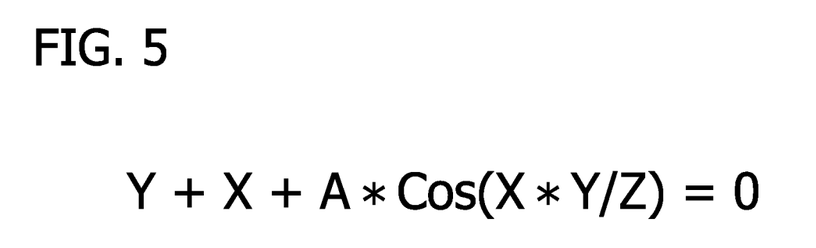
FIG. 5 depicts an exemplary equation used to demonstrate aspects of sequentially inferring the dimensions of variables in accordance with one aspect of the present invention.
Figure 6A:
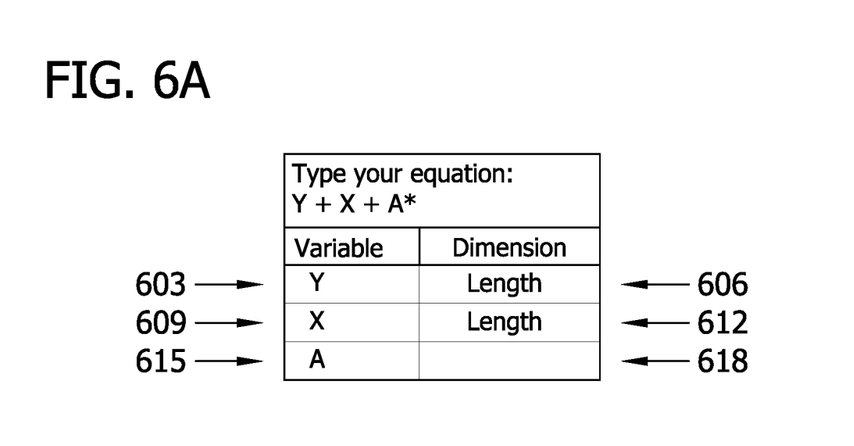
FIGS. 6A-6C depict tables displaying the process of sequentially inferring the dimensions of variables based on user inputs in accordance with one aspect of the present invention.
Figure 6B:
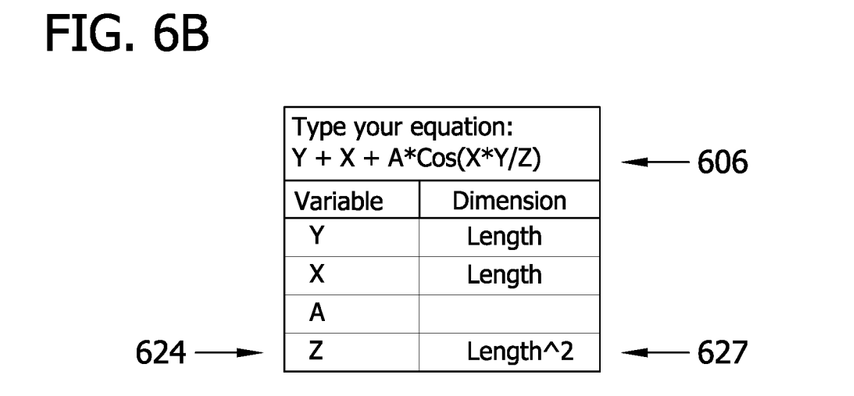
Figure 6C:
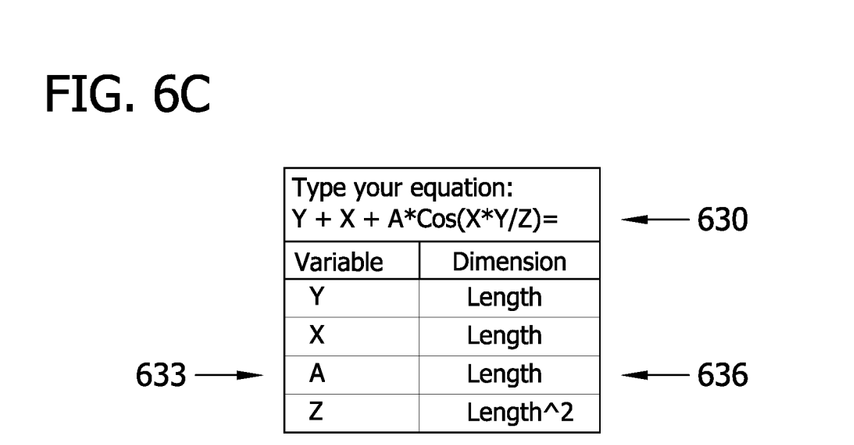

FIG. 5 is an illustration depicting an equation used for purposes of demonstrating aspects of the present invention; in other embodiments, other equations are contemplated for use with the present invention. FIGS. 6A-6C are exemplary depictions of a display resulting from a process by which the dimension of each variable in a user-added equation is automatically determined. For purposes of illustration only, the variable "Y" 603 is a preexisting variable that already exists and has a predetermined dimension of "Length" 606. After the user types "Y+X+", the dimension of the variable "X" is determined to be assignable based upon the preexisting variable "Y", and the dimension "Length" 612 is assigned to the variable "Y". In this instance, additional indications remain related to the creation of a new variable, evident here because the user continues to type the equation in typing "A*", resulting in the entry of variable "A" 615 with an unassigned dimension 618.

With reference to FIG. 6B, entry of the equation continues with the user typing "Cos(X*Y/Z)". The variable "Z" 624 is created and a dimension of "Length^2" 627 is assigned due to the requirement that the argument to a transcendental function (cosine) be dimensionless. Because of the logical relation between dimensions invoked by this requirement, the unassigned dimension of the variable in question becomes assignable.

With reference to FIG. 6C, entry of the equation concludes with the user typing "=" 630. At this point, the variable "A" 633 becomes assignable, due to the requirement that every term in the equation must have the same dimensions. This requirement results in the assignment of a dimension "Length" 636 to variable A.

For purposes of illustration, programs and other executable program components, such as the operating system, are illustrated herein as discrete blocks. It is recognized, however, that such programs and components reside at various times in different storage components of a computing device, and are executed by a data processor(s) of the device.

Although described in connection with an exemplary computing system environment, embodiments of the aspects of the invention are operational with numerous other general purpose or special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well-known computing systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the aspects of the invention may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the invention may also be practiced in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the invention.

Embodiments of the aspects of the invention may be implemented with processor-executable instructions. The processor-executable instructions may be organized into one or more processor-executable components or modules on a tangible processor readable storage medium. Aspects of the invention may be implemented with any number and organization of such components or modules. For example, aspects of the invention are not limited to the specific processor-executable instructions or the specific components or modules illustrated in the figures and described herein. Other embodiments of the aspects of the invention may include different processor-executable instructions or components having more or less functionality than illustrated and described herein.

The order of execution or performance of the operations in embodiments of the aspects of the invention illustrated and described herein is not essential, unless otherwise specified. That is, the operations may be performed in any order, unless otherwise specified, and embodiments of the aspects of the invention may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the aspects of the invention are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the aspects of the invention by way of example and not by way of limitation. This description enables one skilled in the art to make and use the aspects of the invention, and describes several embodiments, adaptations, variations, alternatives and uses of the aspects of the invention, including what is presently believed to be the best mode of carrying out the aspects of the invention. Additionally, it is to be understood that the aspects of the invention is not limited in its application to the details of construction and the arrangement of components set forth in the following description or illustrated in the drawings. The aspects of the invention are capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. It is contemplated that various changes could be made in the above constructions, products, and process without departing from the scope of aspects of the invention. In the preceding specification, various preferred embodiments have been described with reference to the accompanying drawings. It will, however, be evident that various modifications and changes may be made thereto, and additional embodiments may be implemented, without departing from the broader scope of the aspects of the invention as set forth in the claims that follow. The specification and drawings are accordingly to be regarded in an illustrative rather than restrictive sense.

What is claimed is:

1. A system for developing a simulation of a chemical process comprising: a processor;
a memory device coupled to the processor;
an application stored on the memory device and executable by the processor;
a library of equipment models stored on the memory device and accessible by the application; and
instructions stored on the memory device and executable by the processor, wherein said instructions, when executed by the processor, dynamically infer one or more dimensions of variables in a user-added equation to create an updated equipment model, said instructions comprising instructions for:
   selectively presenting an interface to a user;
   receiving, via the interface, a selection of an equipment model for use in developing the simulation;
   determining in response to the received equipment model selection that a corresponding standard equipment model is not present in the library of equipment models accessible by the application;
   receiving, via the interface, an indication of one or more newly added equations for use in the received equipment model selection;
   rendering automatically created variables with unassigned dimensions for the equations in response to the received indication;
   determining whether input is required to assign dimensions to the variables with unassigned dimensions;
   automatically assigning dimensions to the variables with unassigned dimensions when input is not required;
   verifying that each variable in the equations is assigned a dimension;
   transforming the received equipment model selection into the updated equipment model using the equations including the variables with the assigned dimensions; and
   storing the updated equipment model in the library of equipment models.

2. The system of claim 1, wherein the receiving the selection and the receiving the indication comprise input from the user via the interface.

3. The system of claim 2, wherein the determining whether input is required comprises prompting the user via the interface to provide input necessary to assign dimensions to the variables with unassigned dimensions.

4. The system of claim 1, wherein the determining whether input is required and the verifying are based upon logical relations between variable dimensions.

5. A system for developing a simulation of a chemical process comprising: a processor;
a memory device coupled to the processor;
an application stored on the memory device and executable by the processor;
a library of equipment models stored on the memory device and accessible by the application; and
instructions stored on the memory device and executable by the processor, wherein said instructions, when executed by the processor, dynamically infer a dimension for each variable sequentially in a user-added equation to create an updated equipment model, said instructions comprising instructions for:
   receiving, via an interface, a selection of an equipment model for use in developing the simulation;
   determining, in response to the received equipment model indication that a corresponding standard equipment model is not present in the library of equipment models accessible by the application;
   receiving, via the interface, an indication to create a new variable in an equation containing at least one preexisting variable for use in the received equipment model selection, wherein the preexisting variable has a predefined dimension;
   determining whether the dimension of the new variable is assignable based on the preexisting variable;
   assessing whether additional indications remain related to the creation of new variables;
   assigning dimensions to any dimensionless variables remaining in the equation; transforming the received equipment model selection into the updated equipment model using the equation including the variables with the assigned dimensions; and
   storing the updated equipment model in the library of equipment models.

6. The system of claim 5, wherein the determining whether the dimension of the new variable is assignable comprises determining whether any additional variables in the equation are assignable.

7. The system of claim 5, wherein the assessing whether additional indications remain comprises receiving an indication via the interface to create a new variable.

8. The system of claim 5, wherein the indication comprises input received from a user via the interface.

9. A processor executable method for developing a simulation of a chemical process comprising:
   receiving, via an interface, a selection of an equipment model for use in developing the simulation;
   determining in response to the received equipment model selection that a corresponding standard equipment model is not present in a model library;
   receiving, via the interface, an indication of a newly declared, user-added equation for use in the received equipment model selection;
   rendering automatically created variables with unassigned dimensions for the equation in response to the received indication;
   determining whether input is required to assign dimensions to the variables with unassigned dimensions;
   automatically assigning dimensions to the variables with unassigned dimensions when input is not required;
   verifying that each variable in the equation is assigned a dimension, and, transforming the received equipment model selection into an updated equipment model using the equation including the variables with the assigned dimensions;
   and storing the updated equipment model in the model library.

10. The method of claim 9, further comprising:
   receiving, via the interface, an indication of a request for an additional equation related to the newly declared, user-added equation;
   determining whether the additional equation requires the creation of additional variables and rendering automatically created variables with unassigned dimensions in response thereto;
   determining whether input is required to assign dimensions to the additional variables with unassigned dimensions;
   verifying that each variable in the additional equation is assigned a dimension;
   and further transforming the received equipment model selection into the updated equipment model using the additional equation including the additional variables with the assigned dimensions.

11. The method of claim 9, wherein the receiving the selection and the receiving the indication comprise input from a user via the interface.

12. The method of claim 9, wherein the determining whether input is required comprises prompting a user via the interface to provide input necessary to assign dimensions to the variables with unassigned dimensions.

13. The method of claim 9, wherein the determining whether input is required and the verifying are based upon logical relations between variable dimensions.

14. One or more tangible, non-transitory computer-readable media having executable instructions stored thereon that, when executed, perform the method of claim 9.

15. A processor executable method for developing a simulation of a chemical process comprising:
   receiving, via an interface, a selection of an equipment model for use in developing the simulation;
   determining, in response to the received equipment model indication that a corresponding standard equipment model is not present in a library of equipment models accessible by the application;
   receiving an indication, via the interface, to create a new variable in a user-added equation containing at least one preexisting variable for use in the received equipment model selection, wherein the preexisting variable has a predefined dimension;
   determining whether the dimension of the new variable is assignable based on the preexisting variable;
   assessing whether additional indications remain related to the creation of new variables;
   sequentially assigning dimensions to any dimensionless variables remaining in the equation;
   transforming the received equipment model selection into an updated equipment model using the equation including the variables with the assigned dimensions; and
   storing the updated equipment model in the library of equipment models.

16. The method of claim 15, wherein the determining whether the dimension of the new variable is assignable comprises determining whether any additional variables in the equation are assignable.

17. The method of claim 15, wherein the assessing whether additional indications remain comprises receiving an indication via the interface to create a new variable.

18. The method of claim 15, wherein the indication comprises input received from a user via the interface.

19. One or more tangible, non-transitory computer-readable media having executable instructions stored thereon that, when executed, perform the method of claim 15.

* * * * *